United States Patent [19]
Mazzone et al.

[11] Patent Number: 5,900,520
[45] Date of Patent: May 4, 1999

[54] AROMATICS ALKYLATION

[75] Inventors: Dominick N. Mazzone, Wenonah; David O. Marler, Deptford, both of N.J.; Kathleen M. Keville, Beaumont, Tex.; Larry A. Green, Mickleton, N.J.

[73] Assignee: Mobil Oil Corporation, Fairfax, Va.

[21] Appl. No.: 08/376,257

[22] Filed: Jan. 23, 1995

[51] Int. Cl.⁶ .................................................. C07C 2/68
[52] U.S. Cl. ............................................................ 585/467
[58] Field of Search ..................... 585/467, 648, 585/654, 324, 649, 486

[56] References Cited

U.S. PATENT DOCUMENTS

| | | | |
|---|---|---|---|
| 2,904,607 | 9/1959 | Mattox et al. | 260/671 |
| 3,251,897 | 5/1966 | Wise | 260/671 |
| 3,631,120 | 12/1971 | Eberly et al. | 260/671 |
| 3,641,177 | 2/1972 | Eberly et al. | 260/671 C |
| 3,751,504 | 8/1973 | Keown et al. | 260/672 T |
| 3,751,506 | 8/1973 | Burress | 260/671 R |
| 4,301,316 | 11/1981 | Young | 585/455 |
| 4,301,317 | 11/1981 | Young | 585/455 |
| 4,439,409 | 3/1984 | Puppe et al. | 423/328 |
| 4,826,667 | 5/1989 | Zones et al. | 423/277 |
| 4,954,325 | 9/1990 | Rubin et al. | 423/328 |
| 4,954,663 | 9/1990 | Marler et al. | 568/791 |
| 4,962,256 | 10/1990 | Le et al. | 585/467 |
| 4,992,606 | 2/1991 | Kushnerick et al. | 585/467 |
| 5,001,295 | 3/1991 | Angevine et al. | 585/467 |
| 5,043,501 | 8/1991 | Del Rossi et al. | 585/323 |

FOREIGN PATENT DOCUMENTS 0 293 032   5/1987   European Pat. Off. .

*Primary Examiner*—Michael Lewis
*Assistant Examiner*—Tanaga Anne Boozer
*Attorney, Agent, or Firm*—Peter W. Roberts; Malcolm D. Keen

[57] ABSTRACT

Alkyl aromatic compounds are prepared by alkylating an alkylatable aromatic compound with a paraffin alkylating agent under alkylation reaction conditions in the presence of catalyst comprising synthetic porous crystalline material characterized by an X-ray diffraction pattern including interplanar d-spacings at $12.36\pm0.4$, $11.03\pm0.2$, $8.83\pm0.14$, $6.18\pm0.12$, $6.00\pm0.10$, $4.06\pm0.07$, $3.91\pm0.07$, and $3.42\pm0.06$ Angstroms.

25 Claims, No Drawings

AROMATICS ALKYLATION

BACKGROUND OF THE INVENTION

This invention relates to a process for preparing alkyl aromatic compounds by alkylating an aromatic compound with a paraffin alkylating agent employing an alkylation catalyst comprising synthetic porous crystalline material from a particular class of materials characterized by an X-ray powder diffraction pattern including interplanar d-spacings at 12.36±0.4, 11.03±0.2, 8.83±0.14, 6.18±0.12, 6.00±0.10, 4.06±0.07, 3.91±0.07, and 3.42±0.06 Angstroms.

In recent years there has been a dramatic increase in federal and state mandated changes aimed at altering the composition of liquid fuels. Part of this is a reduction in the Reid Vapor Pressure (RVP) for gasoline. In order to meet these RVP specifications, refiners will be forced to remove light paraffins, primarily linear butane and pentane, from the gasoline pool. There are a limited number of process technologies which can be utilized to upgrade these light paraffins. Conventional dehydrogenation routes to produce olefins are extremely capital intensive, cracking processes yield lower molecular weight hydrocarbons as by-products, and M2-Forming produces aromatics whose content in the gasoline pool is being reduced. Isomerization upgrades the octane value of paraffins, but this is accompanied by a corresponding debit, i.e., increase, in RVP number.

The primary use of isoparaffins in a refinery would be in the isoparaffin-olefin alkylation process. However, the volume of paraffins that will be required to be backed out of the gasoline pool will greatly exceed the volume that can be handled without large expansions of alkylation units. Clearly there is a need to develop alternative technologies for upgrading light paraffins.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195) ;zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

U.S. Pat. No. 4,439,409 refers to a composition of matter named PSH-3 and its synthesis from a reaction mixture containing hexamethyleneimine. A composition of matter appearing to be identical to the PSH-3 of U.S. Pat. No. 4,439,409, but with additional structural components, is taught in European Patent Application 293,032. Hexamethyleneimine is also used for synthesis of MCM-22 in U.S. Pat. No. 4,954,325; MCM-35 in U.S. Pat. No. 4,981,663; and a ZSM-12 material in U.S. Pat. No. 5,021,141. A composition of matter referred to as zeolite SSZ-25 is taught in U.S. Pat. No. 4,826,667 and European Patent Application 231,860, said zeolite being synthesized from a reaction mixture containing an adamantane quaternary ammonium ion.

The alkylation of aromatic hydrocarbons with an olefin in the presence of a zeolite having uniform pore openings of from about 6 to about 15 Angstrom units is described in U.S. Pat. No. 2,904,607. U.S. Pat. No. 3,251,897 describes the alkylation of aromatic hydrocarbons in the presence of X- or Y-type zeolites, specifically such zeolites wherein the cation is a rare earth metal species and/or hydrogen. U.S. Pat. Nos. 3,751,504 and 3,751,506 describe the vapor phase alkylation of aromatic hydrocarbons with olefins, e.g., benzene with ethylene, in the presence of catalyst comprising, for example, ZSM-5.

U.S. Pat. Nos. 3,631,120 and 3,641,177, describe a liquid phase process for the alkylation of aromatic hydrocarbons with olefins in the presence of certain zeolites.

U.S. Pat. Nos. 4,301,316 and 4,301,317 disclose the use of such zeolites as ZSM-4, ZSM-20, ZSM-38, mazzite, Linde Type L and zeolite Beta to catalyze the alkylation of benzene with relatively long chain olefins to produce long chain alkylbenzenes.

U.S. Pat. Nos. 4,962,256; 4,992,606; 4,954,663; 5,001,295; and 5,043,501, each incorporated herein by reference in its entirety, teach alkylation of aromatic compounds with various alkylating agents over catalyst comprising a particular crystalline material, such as PSH-3 or MCM-22. U.S. Pat. No. 4,962,256 describes preparing long chain alkylaromatic compounds by alkylating an aromatic compound with a long chain alkylating agent. U.S. Pat. No. 4,992,606 describes preparing short chain alkylaromatics by alkylating an aromatic compound with a short chain alkylating agent. U.S. Pat. No. 4,954,663 teaches alkylation of phenols, and U.S. Pat. No. 5,001,295 teaches alkylation of naphthalene. U.S. Pat. No. 5,043,501 describes preparation of 2,6-dimethylnaphthalene. The alkylating agents taught for use in these patents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

SUMMARY OF THE INVENTION

It is an object of this invention to provide a process for the alkylation of an aromatic compound with a paraffin alkylating agent to produce alkyl aromatic product employing an alkylation catalyst comprising a particular, porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07, and 3.42±0.06 Angstroms.

It is a particular object of the present invention to provide a process for reducing benzene levels in the gasoline inventory by alkylation with an alkylating agent comprising low molecular weight paraffins, such as, for example, those of five carbon atoms or less, e.g., propane, butane, or pentane.

It is another particular object of the invention to improve light cycle oil quality by alkylation with an alkylating agent comprising paraffins of 1 to about 14 carbon atoms to provide product with improved cetane number or increased boiling point into the lubricant range.

It is still another particular object of the present invention to enable a two-stage process involving the present alkylation process, followed by side-chain cracking to produce olefins.

By way of realizing the foregoing and other objects of the invention, a process for preparing alkyl aromatic compounds is provided which comprises contacting at least one alkylatable aromatic compound with at least one paraffin alkylating agent under alkylation reaction conditions and in the presence of an alkylation catalyst to provide an alkylated aromatic product possessing at least one alkyl group derived from said paraffin alkylating agent, said catalyst comprising a synthetic porous crystalline material characterized by an X-ray diffraction pattern substantially as set forth hereinafter.

DESCRIPTION OF SPECIFIC EMBODIMENTS

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene and phenanthrene.

Generally the alkyl groups which can be present as substituents on the aromatic compound contain from one to about 22 carbon atoms and usually from about one to eight carbon atoms, and most usually from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention.

The alkylating agents which are useful in the process of this invention generally include paraffins having from about 1 to about 14 carbon atoms, preferably from about 1 to about 8 carbon atoms. Non-limiting examples of suitable alkylating agents are propane, butanes, pentanes, hexanes, heptanes, octanes and mixtures thereof. Branched alkylating agents, especially isobutane and isopentane, are also useful herein.

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, I/Io × 100 |
|---|---|
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | M–S |
| 3.91 ± 0.07 | M–VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, I/Io × 100 |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | M–S |
| 3.91 ± 0.07 | M–VS |
| 3.42 ± 0.06 | VS |

More specifically, the calcined form may be characterized by an X-ray diffraction pattern including the following lines:

TABLE C

| Interplanar d-Spacing (A) | Relative Intensity, I/Io × 100 |
|---|---|
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | M–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, I/Io × 100 |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | M–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |

TABLE D-continued

| Interplanar d-Spacing (A) | Relative Intensity, I/Io × 100 |
|---|---|
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/$I_o$, where $I_o$ is the intensity of the strongest line or peak, and d (obs.) the interplanar spacing in Angstrom units (A), corresponding to the recorded lines, were determined. In Tables A–D, the relative intensities are given in terms of the symbols W=weak, M=medium, S=strong, and VS=very strong. In terms of intensities, these may be generally designated as follows:

W=0–20
M=20–40
S=40–60
VS=60–100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g., silicon to aluminum ratio of the particular sample, as well as its degree of thermal treatment.

Examples of such porous crystalline materials include the PSH-3 composition of U.S. Pat. No. 4,439,409, incorporated herein by reference, and MCM-22 of U.S. Pat. No. 4,954,325, incorporated herein by reference.

The alkylation catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinum halides and various compounds containing the platinum ammine complex.

The zeolite for use herein, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the alkylation process of this invention, the zeolite crystals should be dehydrated, at least partially. This can be done by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

It may be desired to incorporate the zeolite for use herein with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the zeolite for use herein may be increased, by, for example, combining the as-synthesized zeolite with an alumina binder, converting the alumina-bound zeolite to the hydrogen form, and steaming the alumina-bound zeolite composition under conditions sufficient to increase the stability of the catalyst. U.S. Pat. Nos. 4,663,492; 4,594,146; 4,522,929; and, 4,429,176, the entire disclosures of which are incorporated herein by reference, describe conditions for the steam stabilization of zeolite catalysts which can be utilized to steam-stabilize the present catalyst. The steam stabilization conditions include contacting the alumina-bound zeolite with, e.g., 5–100% steam at a temperature of at least about 300° C. (e.g., 300–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

The alkylation process of this invention is conducted such that the organic reactants, i.e., the alkylatable aromatic compound and the paraffin alkylating agent, are brought into contact with the catalyst composition in a suitable reaction zone such as, for example, in a flow reactor containing a fixed bed of the catalyst composition, under effective alkylation conditions. Such conditions include a temperature of from about 0° C. to about 500° C., a pressure of from about 0.2 to about 250 atmospheres, a feed weight hourly space velocity (WHSV) of from about 0.1 hr$^{-1}$ to about 500 hr$^{-1}$ and an alkylatable aromatic compound to alkylating agent mole ratio of from about 0.1:1 to about 50:1. The WHSV is based upon the weight of the catalyst composition employed, i.e., the total weight of active catalyst (and binder if present). Preferred reaction conditions include a temperature within the approximate range of from about 100° C. to about 450° C., a pressure of from about 1 to about 25 atmospheres, a WHSV of from about 0.5 to about 100 hr$^{-1}$ and an alkylatable aromatic compound to alkylating agent mole ratio of from about 0.5:1 to about 5:1. The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

The alkylation process described herein can be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

As an embodiment of the present invention, benzene levels in gasoline inventory are reduced by contacting the gasoline stream with a $C_1$–$C_5$ paraffin stream in, for example, a 1:5 molar ratio over catalyst comprising MCM-22 at, for example, about 315° C., 500 psig, 1 hr$^{-1}$ WHSV, and 0.5 $H_2$/paraffin molar ratio. The resultant alkylated product will contain a lower benzene level due to ring alkylation by the paraffin.

Another particularly useful embodiment of the present invention results in improved light cycle oil (LCO) quality. This is accomplished by contacting LCO with a $C_1$–$C_{14}$ paraffin in, for example, a 1:5 molar ratio over catalyst comprising MCM-22 at, for example, about 315° C., 500 psig, 1 hr$^{-1}$ WHSV, and 2:1 H$_2$/paraffin ratio. Alklyation with C$_1$-C$_6$ paraffins will result in improved distillate cetane values while reaction with the higher molecular weight paraffins can produce a lubricant range material, potentiallly removing the need for further hydrotreating of the hydrocarbon stream.

Another embodiment of the present invention involves following a first-stage alkylation as described above with a second-stage side-chain cracking process to produce olefins. The second stage involves treating the alkylated aromatic product stream in a fixed- or moving-bed cracking catalyst system at from about 100° to about 600° C., preferably from about 150 to about 450° C., 0.1 to about 20 hr$^{-1}$ WHSV, preferably from about 1 to about 10 hr$^{-1}$ WHSV, 0 to about 250 psig, preferably 0 to about 50 psig, and preferably with no added hydrogen to produce aromatics, olefins, and hydrogen. The hydrogen may be recovered for use in hydroprocessing applications and the olefin may be utilized in numerous upgrading processes. The aromatics can then be recycled to the first stage for re-alkylation.

The cracking catalyst for the side chain cracking process comprises an active component which has cracking activity and which has a pore opening of greater than about 7 Angstroms in effective diameter. The active component may be a conventional large-pore molecular sieve including zeolite X (U.S. Pat. No. 2,882,442); REX; zeolite Y (U.S. Pat. No. 3,130,007); Ultrastable Y (USY) (U.S. Pat. No. 3,449,070); Rare Earth exchanged Y (REY) (U.S. Pat. No. 4,415,438); Rare Earth exchanged USY (REUSY); Dealuminated Y (DeAl Y) (U.S. Pat. No. 3,442,792 and 4,331,694); Ultrahydrophobic Y (UHPY) (U.S. Pat. No. 4,401,556); and/or dealuminated silicon-enriched zeolites, e.g., LZ-210 (U.S. Pat. No. 4,678,765). Preferred are higher silica forms of zeolite Y. ZSM-20 (U.S. Pat. No. 3,972,983); zeolite Beta (U.S. Pat. No. 3,308,069); zeolite L (U.S. Pat. Nos. 3,216,789 and 4,701,315); and naturally occurring zeolites such as faujasite, mordenite, and the like may also be used. Combinations of these molecular sieve materials may also be used. These materials may be subjected to conventional treatments, such as impregnation or ion exchange with rare earths to increase stability. The preferred molecular sieve of those listed above is a zeolite Y, more preferably an REY, USY, or REUSY. These above patents are incorporated herein by reference.

In order to more fully illustrate the nature of the invention and the manner of practicing same, the following examples are presented.

EXAMPLE 1

To prepare a 65% MCM-22/35% alumina-bound catalyst for use herein, a sample of as-synthesized MCM-22 was washed with deionized water and dried at 120° C. A portion of the resultant crystals was combined with Al$_2$O$_3$ to form a mixture of 65 parts, by weight, MCM-22 and 35 parts alumina. Sufficient water was added to this mixture to allow the resulting catalyst to be formed into extrudates. The catalyst was calcined at 482° C. in nitrogen followed by 6 hours in air at 538° C. The calcined extrudate was exchanged with 1 N NH$_4$NO$_3$ for 2 hours at room temperature. The exchanged catalyst was washed with deionized water and the ammonium nitrate/water wash procedure repeated twice. After drying at 120° C., the catalyst particles were calcined for 3 hours at 538° C. in air.

EXAMPLE 2

The catalyst of Example 1 was sized to 14/24 mesh, and 4 grams (8 cc) was loaded into a fixed-bed reactor. The catalyst was dried by flowing 150 cc/minute of nitrogen for 3 hours at 260° C. and 800 psig. Isobutane was then introduced with an Isco pump at 56 grams/hour for 1 hour, and then the flow rate was reduced to 4 grams/hour. 1-Methylnaphthalene was then introduced at a rate of 4 grams/hour with a Milton Roy Mini-pump. Effective WHSV was 2 hr$^{-1}$ overall. The temperature of the reactor was varied from 367° C. to 454° C. and the pressure was maintained at 1000 psig. Both the liquid and gas products were evaluated with a Hewlett-Packard gas chromatograph equipped with a DB-1 column. Liquid products were further characterized by gas chromatography/mass spectrometry utilizing a Finnigan TSQ70 Triple Quadrupole Mass Spectometer equipped with a Varian Gas Chromatograph with a DB-5 column. The results of the experimental study of this example are shown in Table E. The results are normalized to back out the isobutane in the products.

These results show that under the experimental conditions of this study we have been able to alkylate methylnaphthalene with isobutane and also with lighter C$_1$–C$_3$ paraffin compounds which probably were formed from isobutane cracking and subsequent naphthalene alkylation.

TABLE E

| Temperature, ° C. | 367 | 399 | 427 | 454 |
|---|---|---|---|---|
| Pressure, psig | 1000 | 1000 | 1000 | 1000 |
| Normalized Components, wt. % | | | | |
| C$_1$–C$_2$ | 0.00 | 0.042 | 0.134 | 0.529 |
| C$_3$ | 0.11 | 0.144 | 0.215 | 0.822 |
| i-C$_4$$^-$ | 0.066 | 0.123 | 0.221 | 0.446 |
| Other C$_4$ | 0.072 | 0.179 | 0.350 | 1.151 |
| C$_5$–C$_7$ | 0 | 0.012 | 0.041 | 0.383 |
| C$_8$–C$_{10}$ | 0.127 | 0.455 | 0.343 | 0.323 |
| Naphthalene | 0.161 | 0.516 | 1.164 | 2.171 |
| 2-Methylnaphthalene | 1.954 | 9.699 | 24.026 | 37.887 |
| 1-Methylnaphthalene | 95.507 | 87.43 | 70.893 | 52.058 |
| C$_2$ Naphthalene | 0.219 | 0.567 | 1.053 | 1.633 |
| C$_3$ Naphthalene | 0.083 | 0.176 | 0.200 | 0.286 |
| C$_4$ Naphthalene | 0 | 0.031 | 0.198 | 0.746 |
| butyl-1-Me-Naphthalene | 0.145 | 0.411 | 0.765 | 1.156 |
| Unknown C$_{11}$–C$_{16}$ | 0.557 | 0.200 | 0.383 | 0.391 |
| C$_{16}$$^+$ | 0 | 0.017 | 0.014 | 0.018 |
| 1-methyl-Naphthalene Conv. | 2.238 | 11.445 | 28.181 | 47.270 |
| Total methyl naphthalene Conv. (1 & 2 based) | 0.700 | 2.056 | 4.266 | 9.296 |
| Isobutyl-Me-Naphthalene Selectivity (1 & 2 based) | 20.845 | 20.178 | 18.094 | 12.537 |

What is claimed is:

1. A process for preparing alkyl aromatic compounds which comprises contacting at least one alkylatable aromatic compound with an alkylating agent consisting of paraffin having from about 1 to about 14 carbon atoms under alkylation reaction conditions and in the presence of an alkylation catalyst whereby said alkylatable aromatic compound is alkylated by said paraffin to provide an alkylated aromatic product possessing at least one alkyl group derived from said paraffin, said catalyst comprising synthetic porous crystalline material characterized by an X-ray diffraction pattern including interplanar d-spacing values substantially as set forth in Table A of the specification.

2. The process of claim 1 wherein the synthetic porous crystalline material is characterized by an X-ray diffraction pattern including interplanar d-spacing values substantially as set forth in Table B of the specification.

3. The process of claim 1 wherein the synthetic porous crystalline material is characterized by an X-ray diffraction pattern including interplanar d-spacing values substantially as set forth in Table C of the specification.

4. The process of claim 1 wherein the synthetic porous crystalline material is characterized by an X-ray diffraction pattern including interplanar d-spacing values substantially as set forth in Table D of the specification.

5. The process of claim 1 wherein said synthetic porous crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB, and VIII of the Periodic Table.

6. The process of claim 1 wherein said synthetic porous crystalline material has been thermally treated at a temperature up to about 925° C. in the presence or absence of steam.

7. The process of claim 5 wherein said synthetic porous crystalline material has been thermally treated at a temperature up to about 925° C. in the presence or absence of steam.

8. The process of claim 1 wherein said catalyst comprises a matrix material.

9. The process of claim 8 wherein said matrix material comprises alumina, silica, zirconia, titania, or mixture thereof.

10. The process of claim 8 wherein the catalyst is provided in the form of extrudate, beads or fluidizable microspheres.

11. The process of claim 1 wherein the paraffin alkylating agent contains from about 1 to about 8 carbon atoms.

12. The process of claim 1 wherein the alkylating agent is selected from the group consisting of propane, butanes, pentanes, hexanes, heptanes, octanes, and mixtures thereof.

13. The process of claim 1 wherein the alkylatable aromatic compound is selected from the group consisting of benzene, xylene, toluene, and 1,2,3,5-tetramethylbenzene.

14. The process of claim 1 wherein the alkylatable aromatic compound is selected from the group consisting of naphthalene, anthracene, naphthacene, perylene, coronene, phenanthrene, and alkylated analogs thereof.

15. The process of claim 1 wherein the alkylation reaction conditions include a temperature of from about 0° C. to about 500° C., a pressure of from about 0.2 to about 250 atmospheres, a WHSV of from about 0.1 to 500 $hr^{-1}$ and an alkylatable aromatic compound to alkylating agent mole ratio of from about 0.1:1 to 50:1.

16. The process of claim 1 wherein the alkylation reaction conditions include a temperature of from about 100° C. to 450° C., a pressure of from about 1 to about 25 atmospheres, a WHSV of from about 0.5 to about 100 $hr^{-1}$ and an alkylatable aromatic compound to alkylating agent mole ratio of from about 0.5:1 to about 5:1.

17. A process for alkylating an alkylatable polynuclear aromatic hydrocarbon which comprises contacting the alkylatable polynuclear aromatic hydrocarbon with an alkylating agent consisting of paraffin having from about 1 to about 14 carbon atoms under alkylation reaction conditions and in the presence of an alkylation catalyst whereby said alkylatable aromatic compound is alkylated by said catalyst, said catalyst comprising synthetic porous crystalline material characterized by an X-ray diffraction pattern including interplanar d-spacing values substantially as set forth in Table A of the specification.

18. The process of claim 17 wherein the polynuclear aromatic hydrocarbon is selected from the group consisting of naphthalene, anthracene, perylene, coronene, and phenanthrene, and alkylated analogs thereof.

19. The process of claim 17 wherein the paraffin alkylating agent contains from 1 to about 8 carbons atoms.

20. The process of claim 17 wherein the paraffin alkylating agent is selected from the group consisting of propane, butanes, pentanes, hexanes, heptanes, octanes, and mixtures thereof.

21. The process of claim 1 wherein the alkylated aromatic product is contacted with cracking catalyst at cracking conditions including a temperature of from about 100° C. to about 600° C., a pressure of from 0 to about 250 psig, and a weight hourly space velocity of from 0.1 to about 20 $hr^{-1}$ to produce product comprising aromatics, olefins, and hydrogen.

22. The process of claim 21 wherein said cracking conditions include a temperature of from about 150° C. to about 450° C., a pressure of from 0 to about 50 psig, and a weight hourly space velocity of from 1 to about 10 $hr^{-1}$.

23. The process of claim 21 wherein said cracking catalyst comprises a large-pore molecular sieve selected from the group consisting of zeolites X, REX, Y, USY, REY, REUSY, DeAlY, UHPY, LZ-210, ZSM-20, Beta, L, and combinations thereof.

24. The process of claim 21 wherein the paraffin alkylating agent contains from 1 to about 8 carbon atoms.

25. The process of claim 21 wherein the paraffin alkylating agent is selected from the group consisting of propane, butanes, pentanes, hexanes, heptanes, octanes, and mixtures thereof.

* * * * *